(12) United States Patent
Rawert et al.

(10) Patent No.: US 12,194,225 B2
(45) Date of Patent: Jan. 14, 2025

(54) SPRAY NOZZLE FOR AN INHALATION DEVICE

(71) Applicant: INVOX BELGIUM NV, Diepenbeek (BE)

(72) Inventors: Juergen Rawert, Cologne (DE); Frank Bartels, Hattingen (DE)

(73) Assignee: INVOX BELGIUM NV, Diepenbeek (BE)

( * ) Notice: Subject to any disclaimer, the term of this patent is extended or adjusted under 35 U.S.C. 154(b) by 1044 days.

(21) Appl. No.: 16/982,064

(22) PCT Filed: Mar. 19, 2019

(86) PCT No.: PCT/EP2019/056844
§ 371 (c)(1),
(2) Date: Sep. 18, 2020

(87) PCT Pub. No.: WO2019/180022
PCT Pub. Date: Sep. 26, 2019

(65) Prior Publication Data
US 2021/0093802 A1    Apr. 1, 2021

Related U.S. Application Data

(60) Provisional application No. 62/646,193, filed on Mar. 21, 2018.

(30) Foreign Application Priority Data

Mar. 21, 2018  (EP) ...................................... 18163039

(51) Int. Cl.
*A61M 11/00*     (2006.01)
*B05B 1/26*      (2006.01)

(52) U.S. Cl.
CPC .............. *A61M 11/00* (2013.01); *B05B 1/26* (2013.01); *A61M 2207/00* (2013.01)

(58) Field of Classification Search
CPC .... B05B 1/02; B05B 1/00; B05B 1/08; B05B 1/14; B05B 1/26; B05B 1/34; B05B 1/40;
(Continued)

(56) References Cited

U.S. PATENT DOCUMENTS

2007/0063076 A1* 3/2007 Gopalan .................... B05B 1/08
                                                 239/589.1
2007/0131801 A1* 6/2007 Hedger ...................... B05B 1/26
                                                   239/543
(Continued)

FOREIGN PATENT DOCUMENTS

CN    101321551        12/2008
CN    101394932 A       3/2009
(Continued)

OTHER PUBLICATIONS

Written Opinion of the International Application No. PCT/EP2019/056844, May 29, 2019, 10 pages.

*Primary Examiner* — Joseph D. Boecker
*Assistant Examiner* — Brian T Khong
(74) *Attorney, Agent, or Firm* — Synergy IP Group AG (57) ABSTRACT

The invention relates to the field of inhalation devices for liquids. In particular, the invention relates to a nebulizing nozzle to be used in such an inhalation device, as well as a method for fabrication of such a nozzle. A nozzle for an inhalation device for nebulizing a liquid into a respirable aerosol has a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point. The nozzle is characterized in that at least one recess (3) is provided at the front end (1B) in which the channel exits (2A, 2A') are positioned. Disclosed is also a method for the fabrication of a nozzle body as defined above, use of such a nozzle in an inhalation device for nebulizing a liquid, and an inhalation device for nebulizing a liquid into a respirable aerosol, comprising such a nozzle.

17 Claims, 6 Drawing Sheets

(58) Field of Classification Search
CPC .... B05B 1/0425; B05B 1/3405; A61M 11/00;
A61M 11/001; A61M 11/002; A61M
11/02; A61M 11/006; A61M 11/007;
A61M 11/005; Y10T 29/49432
See application file for complete search history.

(56) References Cited

U.S. PATENT DOCUMENTS

| | | | |
|---|---|---|---|
| 2007/0210029 A1* | 9/2007 | Spitz | B05B 1/14 |
| | | | 216/33 |
| 2007/0240714 A1* | 10/2007 | Dunne | A61M 15/002 |
| | | | 128/203.15 |
| 2011/0049262 A1* | 3/2011 | Wissink | B05B 1/26 |
| | | | 239/128 |
| 2014/0145009 A1 | 5/2014 | Hartranft et al. | |

FOREIGN PATENT DOCUMENTS

| | | |
|---|---|---|
| CN | 104225704 A | 12/2014 |
| CN | 105209096 A | 12/2015 |
| EP | 0627230 B1 | 2/2000 |
| EP | 1273355 A1 | 1/2003 |
| EP | 1792660 A1 | 6/2007 |
| EP | 3097981 A1 | 11/2016 |
| EP | 17168869 | 11/2018 |
| GB | 2466631 A | 7/2010 |
| JP | H1176871 A | 3/1999 |
| JP | 2009517146 | 4/2009 |
| RU | 2495726 C2 | 10/2013 |
| WO | 9407607 A1 | 4/1994 |
| WO | 2009090084 A1 | 7/2009 |
| WO | 2016075433 A1 | 5/2016 |

\* cited by examiner

SPRAY NOZZLE FOR AN INHALATION DEVICE

CROSS REFERENCE TO RELATED APPLICATIONS

This application is a United States National Stage Application filed under 35 U.S.C. § 371 claiming priority to and the benefit of PCT Application No. PCT/EP2019/056844, filed on Mar. 19, 2019, which claims priority to and the benefit of European Application No. 18163039.3, filed on Mar. 21, 2018, and U.S. Provisional Application Ser. No. 62/646,193, filed on Mar. 21, 2018, all of which are incorporated herein by reference in their entireties.

The invention relates to the field of inhalation devices for liquids. In particular, the invention relates to a nebulizing nozzle to be used in such an inhalation device, as well as a method for fabrication of such a nozzle.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

An improvement of such an inhalation device is disclosed in patent application EP 17168869, filed by the same applicant as the present invention, the content of which is incorporated herein in its entirety.

In order to achieve a sufficiently homogenous and fine mist of liquid droplets, usually, relatively high pressures such as 10 bar, up to 1000 bar, are necessary. In order to keep the amount of vaporized liquid for each dose acceptably low, the nebulizing nozzle comprises usually one or several channels, each having a cross section only in the order of several $\mu m^2$, e.g. from 2 $\mu m^2$ to 200 $\mu m^2$. The channels are present in a nozzle body, and are often fabricated using micro technological fabrication techniques such as micro etching, micro lithography and the like. However, these techniques are often targeted at hard and brittle materials such as silicon, glass or metal, and in order to avoid any undesired deformation of the nozzle when being subjected to said high pressures, the nozzle is often made from a very rigid material.

The nozzle is therefore usually held in a metallic housing which protects the nozzle during assembly and use. Although often, the term "nozzle" is used for the housing and the part which forms the actual nozzle together, in the following, the term "nozzle" and "nozzle body" refers to the "main" part which leads the liquid.

For fabrication of the nozzle from silicon or glass, often, a disc like substrate wafer is masked and irradiated with a large number of two-dimensional contours of the nozzles, or nozzle features such as the channels. Then, by way of selective etching, the contours, and in particular the channels, are vertically etched into the substrate, such that a wafer, carrying tens or hundreds of batch fabricated, semi-finished nozzles is present. In a separating step, the wafer is cut by way of sawing by a wafer saw into pieces which represent the individual nozzles.

However, if the alignment of the sawing machine with respect to the nozzles is not extremely precise (or even changes during the sawing process), the lengths of the channels are negatively affected. Within one nozzle, if the angle of the saw is not precisely oriented perpendicular to the longitudinal axis of the nozzle, the two (or more) channels have different lengths, since the front edge of the nozzle is not perpendicular to the (usually present) symmetry and longitudinal axis of the nozzle. Furthermore, the mean length of all channels of one nozzle varies from one to the next, so that a very non-uniform output of nozzles is the undesired result.

Another problem arises from possible break-out of small chips of material during sawing. This results in non-uniform, "fringed" channel exits, leading to a less-than-optimal jet, and therefore, droplet formation.

Yet another problem results from damage of the channel exits while assembling the nozzle, during use, or from contamination during fabrication, use, and storage. Dust or fingerprints can clog the exits, resulting in a suboptimal vaporization of liquid due to non-uniform jet formation.

SUMMARY OF THE INVENTION

In a first aspect, the present invention provides a nozzle for an inhalation device for nebulizing a liquid into a respirable aerosol, with a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), wherein further, a lid (4) is provided that covers the at least two channels (2, 2'), and which has a front end (4B) that is, in a view perpendicular to a longitudinal axis (X) of the nozzle body (1), congruent with the front end (1B) of the nozzle body (1), and wherein said recess (3) has a first depth (D') which is larger than the depth (D) of said at least two channels (2, 2').

In a second aspect the present invention provides a method for the fabrication of a nozzle according to the first aspect of the invention, the method comprising the steps of a) providing a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), comprising the following steps:
   providing a wafer substrate;
   fabricating on one side (1A) of said substrate at least two liquid channels (2, 2'), said channels (2, 2') having a defined depth (D);
   fabricating a recess (3) with a first depth (D') which is larger than the depth (D) of said at least two liquid channels (2, 2') in said one side (1A) of the body (1), said recess covering an end portion of the channels (2, 2');

separating said body (1) from the substrate along a separation line (5) which crosses said recess (3); such that at least two channel exits (2B, 2B') in said recess (3) are obtained, wherein the distance between said channel exits (2A, 2A') remains unaffected by a possible angular or linear deviation of said separation line (5) from an optimal separation line (5'), and b) covering said nozzle body (1) with a lid (4).

In further aspects, the present invention provides the nozzle according to the first aspect of the invention, obtained or obtainable by a process according to the second aspect of the invention as well as the use of a nozzle according to the first aspect of the invention in an inhalation device for nebulizing a liquid into a respirable aerosol.

In yet a further aspect, the present invention provides an inhalation device for nebulizing a liquid into a respirable aerosol, comprising a nozzle according to the first aspect of the invention.

Object of the Invention

The object of the invention is the provision of a nozzle that avoids one or more of the drawbacks of the known art.

A further object is the provision of a method for fabricating a nozzle or nozzle body which ensures that when the nozzle body is separated from a wafer, the relative position or the quality of the channel exits is not affected by the separation process.

When separated from a wafer, for a nozzle with channels that are symmetric with respect to a longitudinal axis of the nozzle, and/or that have specific lengths, said symmetry and/or said lengths shall not be affected by the separation process.

When batch-fabricated, the channel lengths of all nozzles from a batch shall have the desired measure, irrespective of slight misalignments of a wafer saw.

During fabrication, use, or storage, the risk of damage or contamination of the susceptible channel exits shall be reduced.

DESCRIPTION OF THE INVENTION

The object is solved by providing a nozzle for an inhalation device for nebulizing a liquid into a respirable aerosol, with a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), wherein further, a lid (4) is provided that covers the at least two channels (2, 2'), and which has a front end (4B) that is, in a view perpendicular to a longitudinal axis (X) of the nozzle body (1), congruent with the front end (1B) of the nozzle body (1), and wherein said recess (3) has a first depth (D') which is larger than the depth (D) of said at least two channels (2, 2').

Furthermore, the object is solved by the method according to the second aspect of the invention. Specific embodiments of the aspects of the present invention are described in the respective dependent claims, the subsequent description, as well as the accompanying figures.

For reference, the nozzle is assumed to have a longitudinal axis (X-axis, X-direction). Distances which, at least mainly, point in this direction are subsequently called "lengths". The term "width" denotes a distance which extends laterally from this X-axis (Y-axis), and the terms "depth" and "height" both denote a distance which stands perpendicular on both aforesaid directions.

The invention relates to a nozzle for an inhalation device for nebulizing a liquid into a respirable aerosol, and in particular, an inhalation device that comprises and makes use of a multi-beam collision nozzle. Such nozzles are characterized in that they comprise a multitude of, specifically at least two, such as two to about five or four, or more specifically two liquid channels from which liquid is emitted at a high velocity. If properly designed and fabricated, the individual jets which run along respective ejection trajectories intersect with one another, forming a fine mist at the collision point.

The nozzle comprises a nozzle body which might be batch-fabricated from a wafer substrate, the substrate typically consisting of a brittle material such as silicon, glass, or ceramics. In further embodiments, it can be made of another material as well, such as a polymeric material, e.g. a thermoplastic polymer such as polyethylene, polypropylene, polystyrene or polyether ether ketone (PEEK) or the like. In further embodiments, the nozzle body can be made of or comprise or consist of a duroplastic material or melamin resins or metals such stainless steel or titanium.

The nozzle body can have a plate-like shape, which typically has dimensions in the centimeter or even millimeter region, such as e.g. a thickness of 1 to 5 mm, a length of 5 to 30 mm, and a width of also 5 to 30 mm.

The nozzle body carries the at least two liquid channels which can be entrenched with a defined depth on one side of said nozzle body. In order to form a collision type nozzle, at least two channels with intersecting jet axes must be present; therefore, if not otherwise stated, the subsequent examples will be based on the assumption that exactly two channels are present in one nozzle. However, the scope of the invention set forth hereinbelow covers in principle also multi-channel nozzles.

According to the invention, a recess is provided at the front end in which at least two of the (possibly more) channel exits are positioned.

Thus, due to said recess, channel exits are provided that are set back with respect to said front end at a certain offset. In other words, at the region where the channels would normally end, i.e. at a region which matches the corresponding contour of the front end, said recess is present.

In one embodiment, this recess laterally extends at least from the outer side of the channel which is the rightmost channel to the outer side of the channel which is the leftmost channel, when "right" and "left" are measured from a longitudinal axis of the nozzle. In a preferred embodiment, the recess extends beyond said outer sides, preferably by at least the same or the same distance corresponding to the difference between the depth of the at least two liquid channels (D) and the first depth (D') of the recess as described in further detail below. The recess has a dimension so as to "cut away" the theoretical foremost portion of each channel (thus shifting position of the channel exits). The depth of the recess (D') is larger than the channel depth (D) to avoid or minimize contact of the jets of liquid ejected from the channels with the surfaces of the recess. By providing the recess, the channel exits are set back into the nozzle such as to be positioned at a rear wall of the recess; the distance (=offset) equals the dimension of the recess 
measured in a direction parallel to the longitudinal axis of the nozzle, from the front end of the nozzle to a "rear wall" of the recess.

The side which carries said channels is typically a "flat" or "top" side of a nozzle body which may have e.g. a plate-like, or cuboidal, overall shape. In the above example, for a nozzle made from a semi-finished product having the size of e.g. about 30 mm×30 mm×5 mm, this would be the side having the larger dimensions (such as e.g. 30 mm×30 mm). In this context, a side which has the smaller dimensions (such as e.g. 30 mm×5 mm) would be called the "front end", denoting the foremost physical portion of the nozzle, and also the rough direction into which a respective liquid jet leaves the channels. Typically, front end and top side are arranged perpendicular to each other.

The jet axis, or ejection trajectory, of each channel (but not necessarily the channel axis itself) crosses said front plane which is congruent with the front end of the nozzle so as to form a "virtual" channel exit in said plane, i.e. the "virtual" position of the channel exit if there were no recess. The term "virtual" indicates that in the present invention and due to the presence of the recess, a "real" channel exit (simply called exit) is present which is situated at a different location.

As a result, when separating the nozzle from the substrate by sawing or laser cutting along a separation line, even if the orientation of said separation line differs from an optimal separation line which runs perpendicular to the longitudinal axis of the nozzle, the distance between the channel exits remains unaffected. Thus, the distance whose precise adjustment is an important measure for obtaining an optimal nebulizing result becomes independent from the orientation of the separation line. This is possible because the exits of the channels become defined by the position of the rear end of the recess which is unaffected by the separation process. This position can be precisely controlled since it is a result of the same precise process which fabricates the channel structures themselves (e.g. masking and selective etching, laser drilling, laser ablating). However, it is not dependent on the separating process which would otherwise (i.e. without the recess) determine the position and orientation of the channel exits which would then be positioned on the (sawed or otherwise separated) front end.

Also, since the channel exits are located in a precisely formed region (the rear wall of the recess) and not the possibly uneven or even "frayed" front end of the nozzle, the jet quality is at a very high level and not influenced by the sawing quality.

Furthermore, looking at adjoining nozzles which are fabricated by a pattern representing a plurality of nozzles and then separated from a single substrate, not only the distance between the channels within each individual nozzle remains constant, but also with regard to all nozzles fabricated from the wafer substrate. Thus, a very homogenous batch can be achieved, resulting in a higher quality and less deviation from the intended design.

A further advantage is that the risk of damage or contamination of the susceptible channel exits is significantly reduced, since—depending on the respective design—the recess can be dimensioned such as to impede touching its back end where the channel exits are located, making it impossible to reach them by accidental touch during use or storage.

According to one embodiment, at least two (or more) recesses are provided; in each one of at least two of these two or more recesses, only one channel exit is located. In further specific embodiments, one individual recess is provided for each channel exit. This means that at each channel exit, an individual recess is present which sets back said exit from the respective front end.

The advantage of this embodiment is that less material must be removed in order to obtain the effect of fabrication independency, and that aforementioned protective effect is further enhanced due to the small size of the recess, in particular when compared to a large single recess for two or more channel exits which are positioned at a relatively large distance to one another.

According to specific embodiments, the nozzle body may be a monolithic structure, or may be obtained from a monolithic structure. This means that the entire nozzle body structure, comprising internal channel structures, is manufactured from bulk material, and no additional part other than a corresponding lid is necessary i.e. to close initially open channel structures, where "open" does of course not refer to the openings that are necessary for proper functioning, such as the channel exits. For example, by way of inscribing channel structures in a block consisting of light sensitive material, and further etching away the illuminated regions, channels can be formed inside said block. With the same process, the recess(es) according to the invention can be fabricated as well.

The nozzle body has a flat side, with the at least two liquid channels being entrenched with a defined depth on said flat side, wherein further, a lid is provided that covers the at least two channels, and which has a front end that is, in a view perpendicular to a longitudinal axis of the nozzle, congruent with the front end of the nozzle body.

In other words, in order to enclose the channels in all lateral directions but not the entry and exit region, a lid is provided that covers the initially open top side of the nozzle body. The lid may be made of the same material as the wafer substrate, but it can be made of another material as well, such as a polymeric material, e.g. a thermoplastic polymer such as polyethylene, polypropylene, polystyrene or polyether ether ketone (PEEK) or the like. In specific embodiments, at least one of the nozzle body and the lid may be formed of PEEK. In further specific embodiments the nozzle body and the lid may be formed of PEEK or, in other words, may comprise or consist of PEEK. In other embodiments, the nozzle body or the lid may be formed of PEEK and the other one may be formed of or may comprise or consist of another material, preferably silicon or glass. In further embodiments, the lid and/or the nozzle body as described above can be made of or comprise or consist of a duroplastic material or melamin resins or metals such stainless steel or titanium.

For example, the substrate can consist of silicon, and the lid can consist of glass or vice versa. The front end of the lid should align with the front end of the nozzle body. In specific embodiments, the front line of the lid and the front line of the nozzle body may be oriented perpendicular to the longitudinal axis of the nozzle body. However, even if this is not the case after connecting the lid with the substrate prior to the individualization of the nozzles, the sawing process may be designed to result in such an alignment.

In specific embodiments, the lid is provided as a possibly pre-structured second substrate which is bonded to the nozzle body substrate. After bonding, the nozzles can be separated. Thus, not all lids must be individually placed and bonded to the substrate, or even on the already individualized nozzle bodies. However, the latter is possible as well.

In further specific embodiments, the lid carries some or all of the structures that the nozzle body carries, but in an inverted pattern. Thus, when the lid is bonded to the nozzle body, both form the liquid structures together. E.g., a side wall of a channel consists of a lower portion which is entrenched in the nozzle body, and a higher portion which is entrenched in the lid. In fact, if the nozzle is designed highly symmetrical with respect to its longitudinal axis, the lid can be provided by a second nozzle body that is placed with its flat side against the flat side of the first nozzle body.

In specific embodiments, the lid may provide an upper portion of the recess, wherein said portion runs from one side of the lid to the other side. In these embodiments, the recess portion may have the shape of a chamfer, with a channel-adjoining edge. In preferred embodiments, said edge is collinear with the respective edges of the channel exits. In this way, a circumferential step may be provided around said channel exits.

An additional advantage that may be associated with these embodiments is that, due to capillary effects, liquid to be ejected from the ejection channels which can accumulate during use of the nozzle around the exits may be transported away from the exits towards the sides of the nozzle.

The recess has a depth (D') which is larger than the depth (D) of said channels. This results in a step being formed at the exit of a channel, said step being also precisely fabricable. In this way, each channel exit has (at least) three sides which provide a high surface quality, namely the right and left side (defined, when looking along the longitudinal axis, by the "width" of the recess), as well as the bottom side (defined, in the same view, by the depth of the recess). This high surface quality would also result in high quality edges at the channel exits, which are also particularly advantageous in that they further contribute to precisely defined, reproducible liquid jets to be emitted from the nozzle under working conditions.

The depth of the recess has the size of the depth of the channels multiplied by a factor of >1. The multiplying factor may, for example, be in the range between 1.1 and 50, and preferably in the range of 1.5 to 30, or in the range of 1.5 to 10 or 1.5 to 5, such as about 3. The difference between the depth of the liquid channels (D) and the depth of the recess (D'), in absolute measures, may be in the range of from about 20 µm to about 400 µm, preferably from about 20 to about 100 µm. Towards the sides, the recess walls can have a distance of e.g. 100 to 150 µm from each channel exit; the length of the recess (offset) can e.g. amount from about 50 to 80 µm.

In specific embodiments, the at least two ejection channels may have a length in the range of from about 20 µm to about 500 µm, or from about 50 µm to about 150 µm, such as about 100 µm. In further specific embodiments, the at least two ejection channels have an equal length. Furthermore, the at least two ejection channels may have a cross section in the range of from about 2 $\mu m^2$ to about 400 $\mu m^2$, or from about 10 $\mu m^2$ to about 100 $\mu m^2$, such as from about 20 $\mu m^2$ to about 50 $\mu m^2$. Preferably, the at least two ejection channels have a cross section which is constant over the whole length of the channel.

Preferably, each channel exit is surrounded, at least in three directions (right, left, downwards), by a symmetric circumferential step. In specific embodiments, the channel exit is surrounded by circumferential step, more specifically a symmetrical circumferential step, in four directions (right, left, downward, upward).

In a preferred embodiment, the aforesaid lid has, at its front end, a portion where the recess extends into the lid. In other words, the lid has also a recess, or shares the recess of the nozzle body. In this way, the advantages of the recess in the nozzle body are "copied" to the lid. In particular, a step completely surrounding the exit of a channel can be provided.

In further specific embodiments, the recess of the lid is, with respect to a plane which is parallel to said one side and which divides the channels in two halves of equal height (central plane), symmetric to the recess of the nozzle body. In this way, the symmetry of said step is increased; the jet is not drawn to one particular side when exiting the channel, because the top and the bottom sides can have same distances to the channel exit.

According to further specific embodiments, said recess may have, seen along the direction of the longitudinal axis, an increasing depth and/or width, such that a sloping cross section is provided, being widest at the front end. In other words, a successively widening and/or deepening cross section of the recess is provided. Such a sloping, widening and/or deepening cross section allows for a particularly smooth transition from the channel exit to the recess walls, providing a "trumpet-like" or "bell-like" region where the liquid jet leaves the channel exit.

Such a cross section can be achieved in successively removing the more material in a direction perpendicular to the one side (i.e. the top side that carries the channels), the closer the front end is. At the channel exits, the depth and width, and therefore removed amount, may be larger than the depth of the channel exit itself, or the outer distance between the channel exits, respectively. The slope can e.g. be linear, exponential, or logarithmic.

In further specific embodiments, the nozzle comprises a plurality of nozzle bodies. These nozzle bodies can be stacked one above another, thus forming a stack of individual nozzle bodies. In these embodiments, each nozzle body may have a front end (1B) and may comprise at least two ejection channels (2, 2'), with each channel (2, 2') having an channel exit (2A, 2A'), wherein the ejection channels (2, 2') are arranged such as to eject liquid along respective ejection trajectories which intersect with one another at a collision point, and at least one recess (3) which is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A).

In specific embodiments, a nozzle with multiple collision points can be obtained, if at least two pairs of jets exist which respectively intersecting ejection trajectories. Each pair can be provided by one "layer", i.e. one nozzle body.

In further specific embodiments, each nozzle body may have its own recess. This means that a plurality of individual recesses may be present, wherein each recess covers only a subset of channels; preferably, this is a subset that consists of the channels of one individual nozzle body ("layer"). The advantage of this embodiment is that the individual recesses can be small, thus increasing the aforementioned protective effect.

In further embodiments, multiple nozzle bodies may share a common recess. This means that a recess extends over more than one nozzle body or layer, thus covering some, or even all of the channel exits. The advantage of this embodiment is that the common recesses may be easier to be fabricated, e.g. in one step after stacking the individual nozzle bodies to form the nozzle.

In further specific embodiment, a side opposite to the flat side of one nozzle body serves as lid for an adjoining nozzle body. In other words, the "top" side of a first nozzle body is closed by the "bottom" side of a second nozzle body.

In this way, only the last (topmost) nozzle body needs to be closed by a specific lid; all other layers are closed by the adjoining layers. This results in a more simple nozzle construction, with less individual parts and process steps.

In a second aspect, the invention also relates to a method for the fabrication of a nozzle according to the first aspect of the invention as defined above, said method comprising the steps of a) providing a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), comprising the following steps:
   providing a wafer substrate;
   fabricating on one side (1A) of said substrate at least two liquid channels (2, 2'), said channels (2, 2') having a defined depth (D);
   fabricating a recess (3) with a first depth (D') which is larger than the depth (D) of said at least two liquid channels (2, 2') in said one side (1A) of the body (1), said recess covering an end portion of the channels (2, 2');
   separating said body (1) from the substrate along a separation line (5) which crosses said recess (3);
   such that at least two channel exits (2B, 2B') in said recess (3) are obtained, wherein the distance between said channel exits (2A, 2A') remains unaffected by a possible angular or linear deviation of said separation line (5) from an optimal separation line (5'), and
b) covering said nozzle body (1) with a lid (4).

As a result, at least two channel exits located in said recess are obtained. Thus, the "rear wall" of the recess defines the position of the channel exits, and not the position or orientation of a separation line along which the nozzle body is separated from the remaining substrate or bulk material. Therefore, the distance between said channel exits remains unaffected by a possible deviation of said separation line from an optimal separation line. Typically, such optimal separation line runs perpendicular to the longitudinal axis of the nozzle body and/or parallel to the front plane (i.e. without an angular or axial offset). In this way, the result of the fabrication process becomes independent of the exact orientation of the sawing line.

It is clear that this independency has its limits, but these limits are usually beyond the precision which is possible to provide by normal efforts with regard to the production process. As an example, looking at a standard wafer having a diameter of 300 mm, and an individual nozzle body dimension of 3 mm×5 mm, and a channel length of 150 μm, measured in direction of the longitudinal axis of the nozzle body, a deviation of the sawing line from the optimal separation line of 1 degree is still tolerable.

In specific embodiments, subsequent to the process steps summarized as step a), said nozzle body (1) is covered with a lid (4) according to step b). For covering said nozzle body, said lid may be placed and attached, or bonded, onto the side of the nozzle body which has the channels.

In further specific embodiments, a substrate carrying a plurality of lids may be placed and bonded onto the structured, but not yet sectioned substrate of the nozzle bodies, and the sectioning takes place after bonding along the separation line.

The lid for covering the nozzle body can be unstructured, or it can be fabricated in the same manner as the nozzle body substrate, i.e. by fabricating channels in one side of the lid. Therefore, by properly aligning body and lid, the channels and recesses in both substrates match, and the result is a nozzle with conduit structures for liquid in both parts of the nozzle. Also, the lid can be a mirrored copy of the body; in other words, by bonding two matching nozzle bodies together, a nozzle can be obtained as well.

In specific embodiments in which a pattern representing a plurality of nozzle bodies is batch fabricated in said wafer substrate, the separation line crosses all recesses that have been formed within the substrate. In these embodiments, not only one single nozzle body, but all adjacent nozzle bodies are separated along a common separation line. Said line crosses all the recesses of all nozzle bodies. Thus, the aforementioned advantage regarding one individual nozzle body is multiplied such that all nozzle bodies have the same geometric dimensions relevant for a homogenous batch quality.

According to specific embodiments, the cannels and/or the recess(es) may be fabricated by way of etching. This fabrication technique is particularly advantageous when a wafer-shaped substrate, preferably wafer substrates of glass or silicon, is used for batch fabrication of a larger quantity of nozzle bodies.

According to another embodiment, the cannels and/or the recess(es) may be fabricated by way of laser drilling and/or laser ablation. This fabrication technique is particularly advantageous if the nozzle body is fabricated from a monolithic block or from other materials as described above in connection with the nozzle body or lid of the first aspect of the invention.

In a third aspect, the invention also relates to a nozzle according to the first aspect of the invention as described above, obtained or obtainable by a process according to the second aspect of the invention. In other words, the invention relates to all nozzles, comprising a nozzle body as defined above, when said nozzle body is fabricated by way of the described process.

In a fourth aspect, the invention relates also to the use of a nozzle according to the first aspect of the invention as described above, in an inhalation device for nebulizing a liquid into a respirable aerosol.

In a fifth aspect, the invention relates to an inhalation device for nebulizing a liquid into a respirable aerosol, comprising a nozzle according to the first aspect of the invention. Accordingly, the present invention also relates to an inhalation device for nebulizing a liquid, preferably a liquid comprising an inhalable active pharmaceutic ingredient (API), into a respirable aerosol comprising a nozzle with a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), wherein further, a lid (4) is provided that covers the at least two channels (2, 2'), and which has a front end (4B) that is, in a view perpendicular to a longitudinal axis (X) of the nozzle body (1), congruent with the front end (1B) of the nozzle body (1), and wherein said recess (3) has a first depth (D') which is larger than the depth (D) of said at least two channels (2, 2').

In order to avoid repetition, reference is made to the above explanations regarding a nozzle, a fabrication method thereof, and an inhalation device comprising such a nozzle, as well to the subsequent description of the figures.

DESCRIPTION OF FIGURES

Subsequently, the invention is exemplified by aid of the following figures. Herein.

Figure 1:
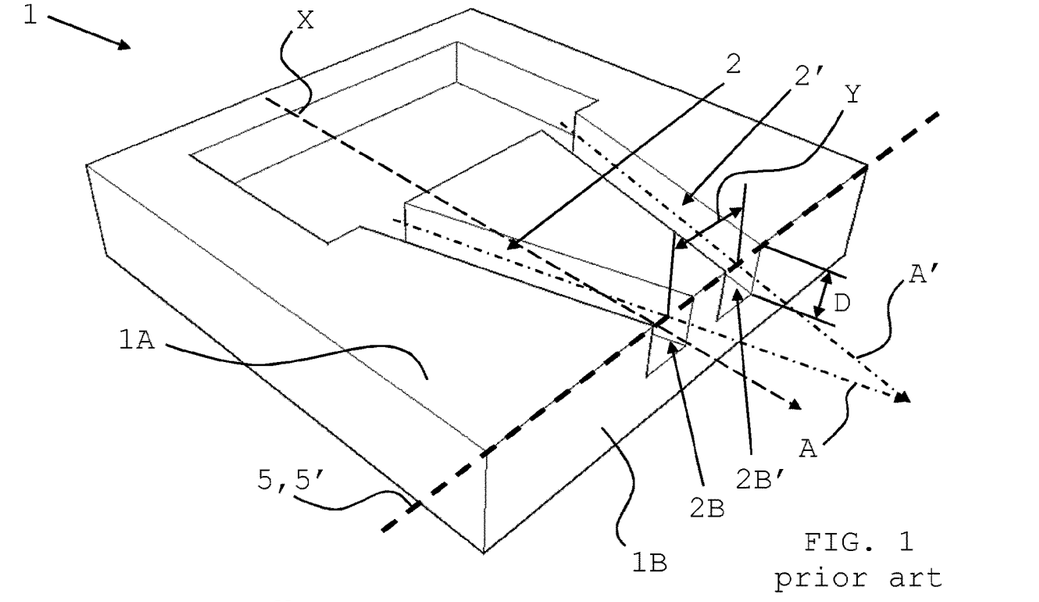
FIG. 1 shows a nozzle body according to the state of the art.

In FIG. 1, a nozzle body 1 according to the state of the art is schematically depicted. The nozzle body 1 has an overall shape of a rectangular cuboid. In a rear section, a collecting chamber is present; however, inlet ducts and the like are omitted in the drawing for the sake of clarity.

Two liquid channels 2, 2' which are entrenched with a certain depth D are present on one flat side 1A of said nozzle body 1. Longitudinal axis X (thin dashed line) runs along the length of the nozzle body 1.

Each jet axis A, A' (dash-dotted line) of each channel 2, 2' crosses a front plane congruent with the front end 1B of the nozzle body 1. In this example, jet axis A, A' is collinear with the respective channel axis (no reference numeral). In FIG. 1, depicting the state of the art, the so formed "front end channel exits" 2B, 2B' are—in the absence of a recess—located in this front plane which is also the front end 1B.

During manufacture, the front end 1B may be generated by sawing, or otherwise separating, the nozzle body 1 from a larger unit (e.g. a wafer) along a separation line 5 (bold dashed line). In the example, this separation line 5 is collinear with an optimal separation line 5'. Therefore, the lateral distance Y of the front end channel exits 2B, 2B', measured between their respective jet axes A, A', is as initially designed or intended.

Figure 2:
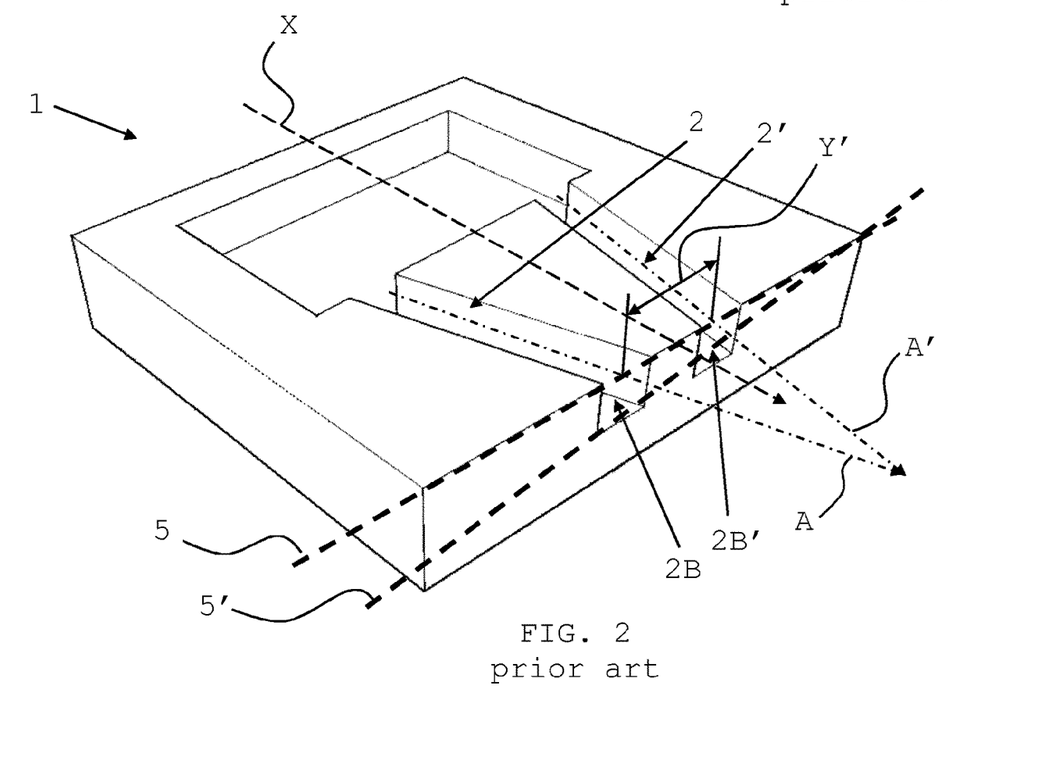
FIG. 2 shows a nozzle body as in FIG. 1, resulting from an angled separation line.

In FIG. 2, a prior art nozzle body as in FIG. 1, but resulting from a non-optimal, angled (with respect to the optimal separation line 5') separation line 5, is depicted. In this figure, some of the already introduced reference numerals are omitted.

As can be seen, due to the angular deviation of the separation line 5 from the optimal separation line 5', the lateral distance Y' of the front end channel exits 2B, 2B', again measured between their respective jet axes A, A' at the respective front end channel exits 2B, 2B', is not as initially designed (in this example, it is larger than intended). Since the front end channel exits 2B, 2B' are now no longer located in the intended plane (front plane in FIG. 1), but in a plane that results from said angular deviation, their respective lengths (no reference numeral) also differ from each other. This might result in suboptimal nebulization. In the example, channel 2 is shorter than channel 2'.

Figure 3:
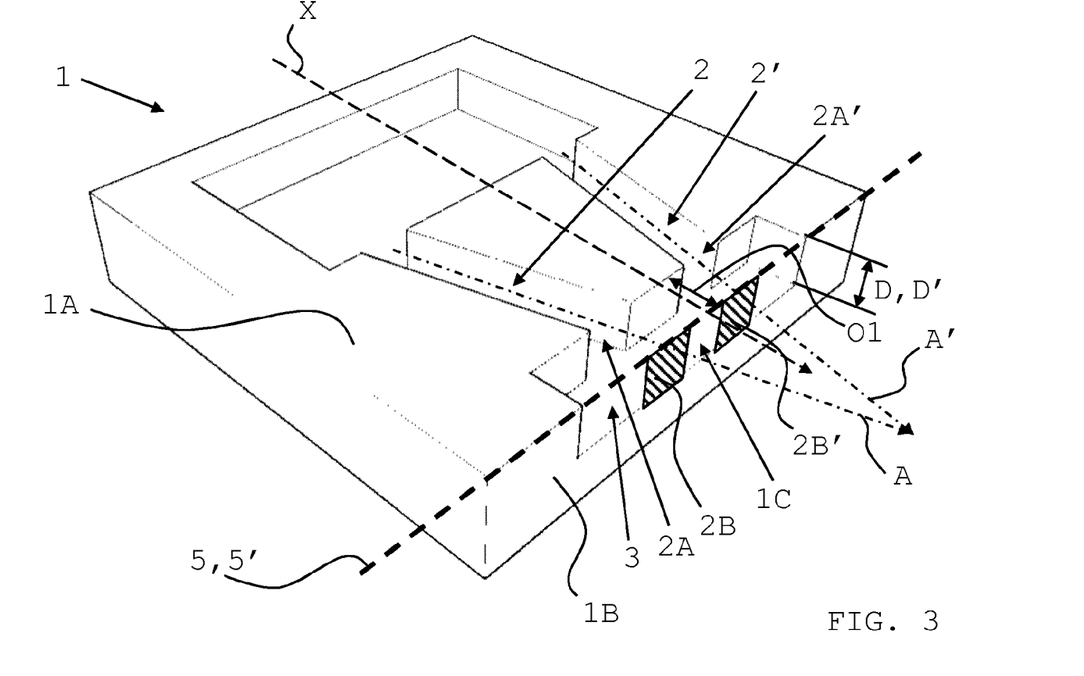
FIG. 3 shows a nozzle body having a recess.
Figure 4:
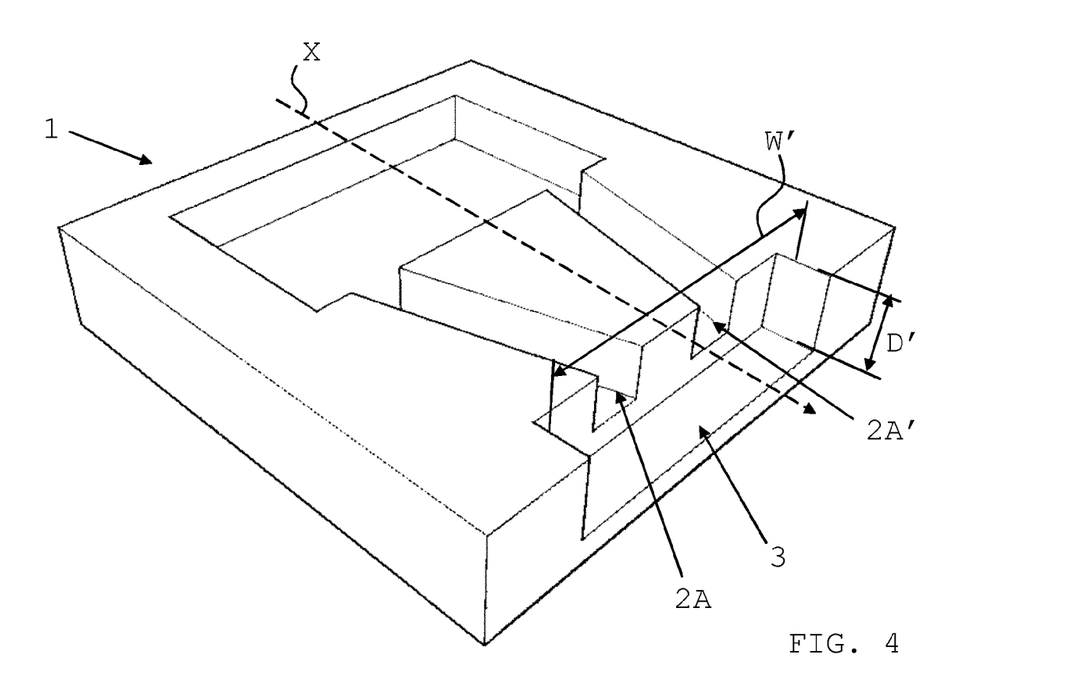
FIG. 4 shows a nozzle body having a recess with an increased depth.
Figure 5:
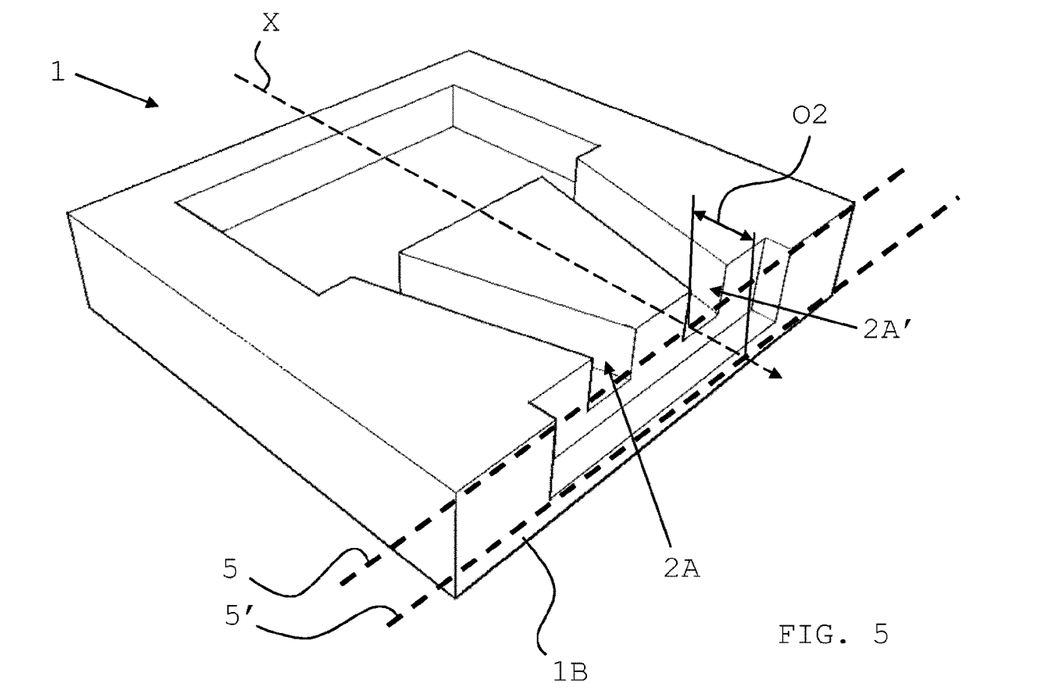
FIG. 5 shows a nozzle body as in FIG. 4 resulting from an offset separation line.

As shown in FIG. 3, an exemplary nozzle body 1 has a recess 3. Recess 3 has a depth D' which is, in this example, equal to the depth D of channels 2, 2'. As the channels 2, 2', recess 3 is provided in said flat side 1A. It is located at the front end 1B of the nozzle body 1, as an indentation of the front end. Thus, recess 3 could be understood as encompassing the (now "virtual") front end channel exits 2B, 2B' (hatched areas) such that ("real") channel exits 2A, 2A' are provided that are set back with respect to said front end 1B at a certain offset O1.

As a result, any potential damages to the front end 1B resulting from separating, such as by mechanically sawing, the nozzle body 1 from a larger unit along the separation line 5' which is, in this example, also the optimal separation line 5, do not affect the channel exits 2A, 2A' since these are never touched by a sawing blade or any other separation tool. Thus, the quality of a liquid jet ejected from such channels during nebulization is also not affected. Even if the surface roughness of the front side 1B is increased due to faster sawing, this will not have a negative influence on the jet quality. Therefore, quicker and/or less costly separation techniques can be used for separating the nozzle body 1 from its substrate.

In FIG. 4, a nozzle body 1 having a recess 3 with an increased depth D' is shown. In this way, a step is present at the exits 2A, 2A' of the channels 2, 2', said step being also precisely fabricable. In the example, each channel exit 2A, 2A' (before adding a counterpart such as a lid) has three sides which can be designed to exhibit a high surface quality, namely the right and left side (defined by the width W' of recess 3), as well as the bottom side (defined by the depth D' of the recess 3). It should be pointed out that for a satisfying jet quality, in particular, the quality of the edges surrounding each channel exit 2A, 2A' must be good; this is true for all embodiments. The advantage of this embodiment is that the liquid jet (not shown) which leaves a channel 2, 2' does not come in contact with any other surfaces or edges which may have lower surface or edge quality, thus ensuring a high quality and reproducibility of nebulization.

FIG. 5 shows a nozzle body 1 as shown in FIG. 4, but in this case, nozzle body 1 was individualized along a separation line 5 which is spaced apart with an offset O2 from the optimal separation line 5', lies in front of the nozzle body 1. As a result, front end 1B of the nozzle body 1 in FIG. 5 is parallel to the one in FIG. 4. Despite this difference, the exits 2A, 2A' have the same, desired distance from each other as in the embodiment of FIG. 4. Thus, the position of the separation line 5 can vary in a certain range without affecting the relevant geometry of the nozzle body 1.

In FIG. 6, a nozzle body similar to the one of FIG. 4 is shown, but in the depicted case, nozzle body 1 was individualized along a separation line 5 which includes a pointed angle α with the optimal separation line 5'. However, again, this deviation does neither affect the length of the channels, nor the distance of their channel exits (respective reference numerals omitted), since recess 3 provides a "buffer" for imprecise orientation of the separation line 5.

Figure 6:
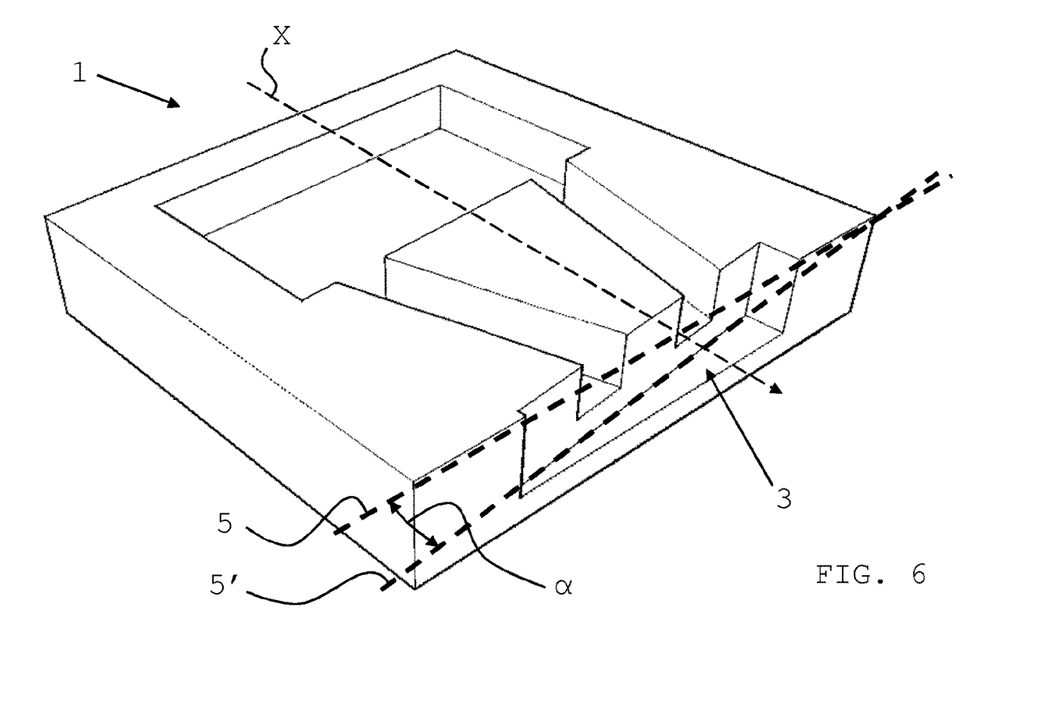
FIG. 6 shows a nozzle body as in FIG. 4 resulting from an angled separation line.

Of course, recess 3 can also compensate the otherwise negative effects of a combination of an angular and offset deviation, as well as any other deviation, as long as the resulting cutting plane lies entirely within recess 3.

Figure 7:
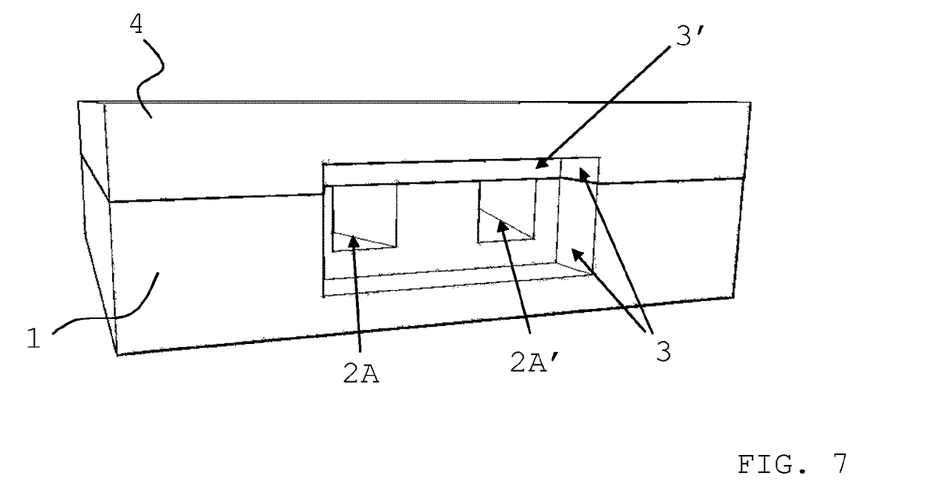
FIG. 7 shows a nozzle body as in FIG. 4, covered by a lid, with a single recess.

In FIG. 7, a nozzle body 1 is shown which is covered by a lid 4. The resulting nozzle comprises a single recess 3 which has a lower portion, located in the nozzle body 1, and an upper portion 3' which is located in the lid 4. As can be seen, a circumferential step is present that surrounds both channel exits 2A, 2A'.

Figure 8:
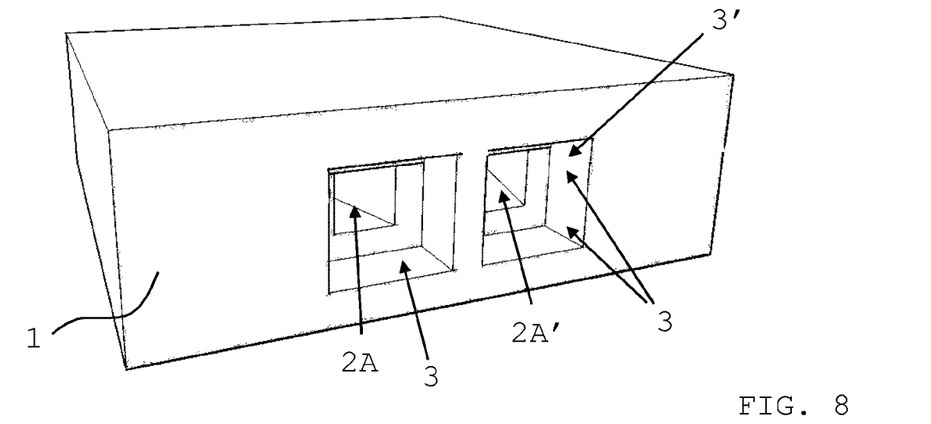
FIG. 8 shows a nozzle body covered by a lid, with two individual recesses.

In contrast, in FIG. 8 shows another nozzle body 1 which may be made from a monolithic structure. Thus, a lid is not necessary. In this embodiment, two individual recesses 3 exist, each surrounding one channel exit 2A and 2A', respectively. It is clear that an embodiment with two recesses is also possible if the nozzle body 1 is designed as shown e.g. in FIG. 7 with "open" channels 2, 2' and a lid 4.

Figure 9:
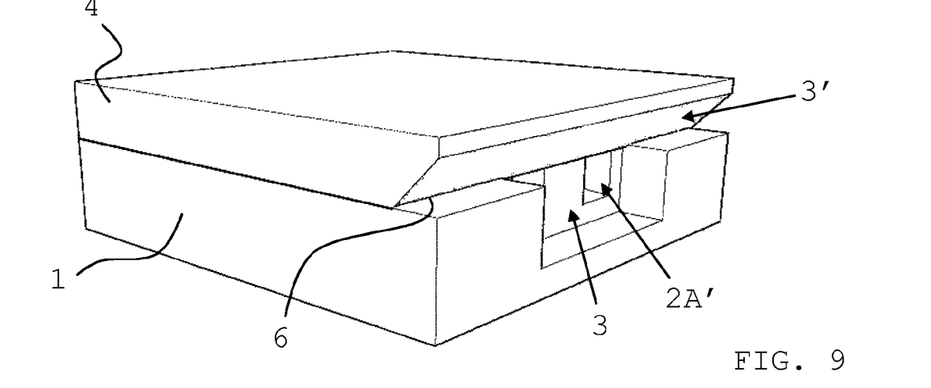
FIG. 9 shows a nozzle body as in FIG. 4, covered by a lid, with a side-to-side recess.

FIG. 9 shows an embodiment with a lid 4 that provides the upper portion 3' of the recess 3, wherein said portion 3' runs from one side of the lid 4 to the other side. The recess portion 3' has the shape of a chamfer, with a channel-adjoining edge 6. As shown, preferably, said edge 6 is collinear with the respective edges of the channel exits 2A, 2A'. In this way, still, a circumferential step is provided around said exits 2A, 2A'.

An additional advantage of said embodiment is that, due to capillary effects, liquid which can accumulate during use of the nozzle around the exits 2A, 2A' is transported away from the exits towards the sides of the nozzle. It is clear that neither the shown angles nor dimensions are drawn to scale; depending on physical parameters such as the viscosity of the liquid, other dimensions can be necessary in order to obtain an optimal result. It is also clear that the slope of the chamfer must be larger than the diameter of the jet in order to avoid collision of the jet with the wall of the portion 3'.

Figure 10:
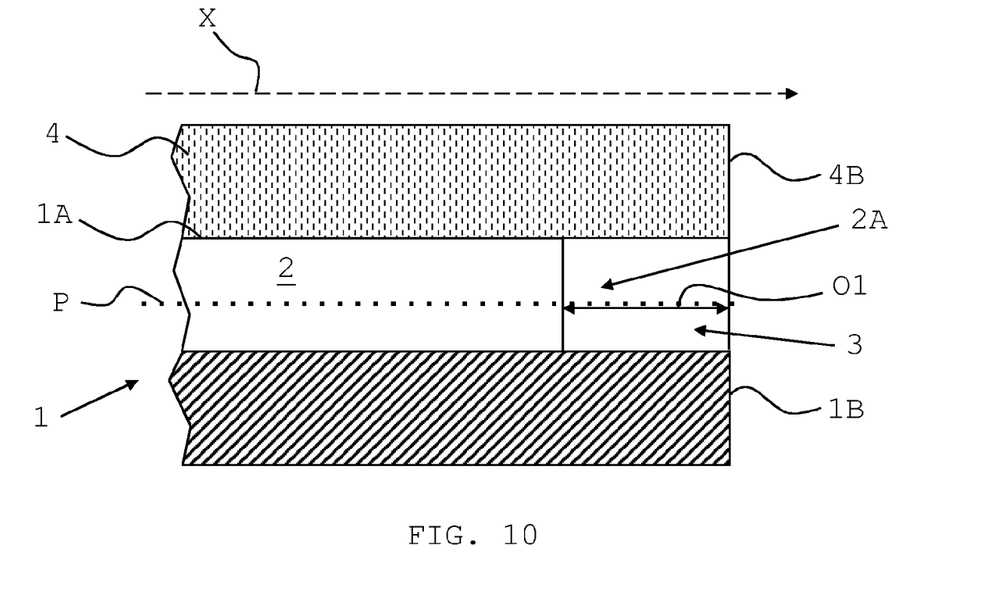
FIG. 10 shows a cut view of a front portion of a nozzle.

In FIG. 10, a cut view of a front portion of a nozzle, based on the embodiment of FIGS. 3 to 6, comprising the nozzle body 1 is shown. In this embodiment, a counterpart in the form of a lid 4 which serves as a cover was placed onto the one side 1A so as to close channels 2, 2' (channel 2' not visible). The cut view goes through the end portion of channel 2 which is therefore drawn without hatching.

Due to recess 3, the channel exit 2A is offset at distance O1 from front end 1B. As can be seen, front end 4B of lid 4 is, in a view perpendicular to a longitudinal axis X (from above in FIG. 7, parallel to the drawing plane), congruent with the front end 1B of the nozzle body 1.

Although non-congruent embodiments are also possible, the embodiment of FIG. 10 is particularly advantageous because it can be achieved by firstly bonding substrate containing a plurality of nozzle bodies and another substrate containing a plurality of lids 4 to each other, and then by separating the initially semi-finished nozzle along a separation line which is perpendicular to the drawing plane in FIG. 10 from its neighboring nozzle (not depicted), such that individualized nozzles are obtained, each comprising a nozzle body and a lid bonded to the same. Since lid substrate and nozzle body substrate are cut in the same workstep, the congruency is produced automatically. An advantage is the symmetric result, since top and bottom sides in front of the channel exits 2A, 2A' are essentially mirror-inverted with one another. Thus, the liquid jet will not deviate in either of these directions.

Figure 11:
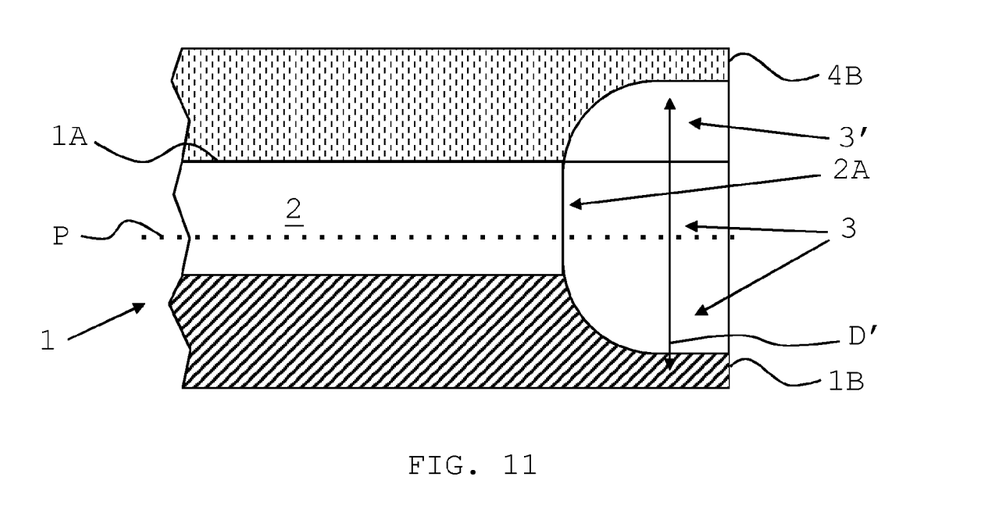
FIG. 11 shows a nozzle with a recess that extends into a lid.

In FIG. 11, a further embodiment of a nozzle comprising a nozzle body 1 and a lid 4 is shown, again with a recess 3 which has a portion 3' which extends into the lid 4, similar to the embodiment shown in FIG. 7. The lower portion of recess 3 is located in nozzle body 1, also enclosing channel 2, whereas upper portion 3' is located in lid 4. In this embodiment, portion 3' is, with respect to a nozzle central plane P (dotted line) which is parallel to said one side 1A, symmetric to the lower portion of recess 3 of nozzle body 1.

Further, and contrary to the situation shown in FIG. 10, in this embodiment, recess 3 has, seen from the channel exits 2A, 2A', an increasing depth D' (measured in vertical direction in FIG. 11), thus enlarging towards the front end 1B, 4B. Optionally, the width may also increase along the same direction. In this way, the shown sloping cross section is provided, being largest at the respective front end 1B, 4B. Such a sloping cross section allows for a particularly smooth transition from the channel exits 2A, 2A' to the recess walls, providing a "bell-like" region where the liquid jet (not shown) leaves each channel exit. As a result, the jet quality is increased.

Figure 12:
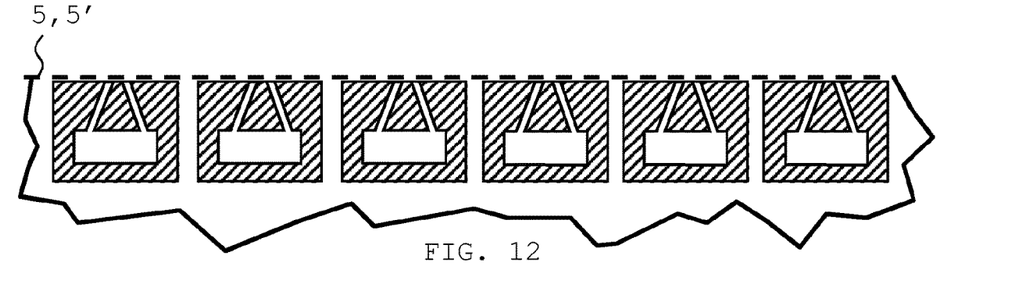
FIG. 12 shows a plurality of prior art nozzle bodies separated from a substrate along an optimal separation line.

FIG. 12 shows schematically a plurality of nozzle bodies from the known art which are just separated from a substrate (not shown) along their respective front ends (reference numerals omitted). The optimal separation line 5' is indicated by the dashed line. As a result, all nozzle bodies are identical; in particular, the distances between the channel exits are identical for all nozzle bodies.

Figure 13:
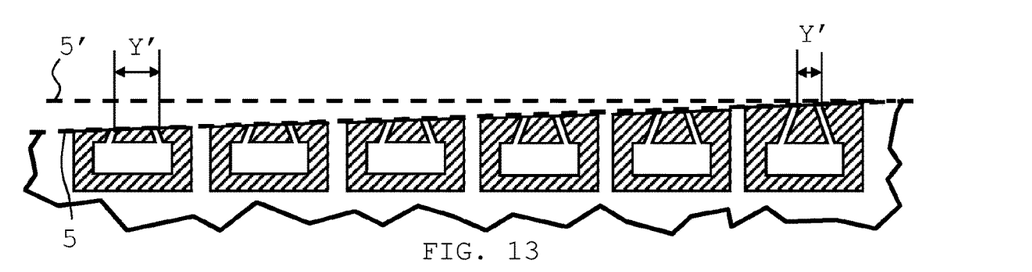
FIG. 13 shows a plurality of prior art nozzle bodies when separated along an angled separation line.

However, if the nozzle bodies are separated along separation line 5, as depicted in FIG. 13, an angular deviation exists which results in a variation of the lateral distances Y' of the channel exits, which is clearly undesired. Also, the respective lengths of both channels of one nozzle body are also slightly different (each left channel is shorter than the respective right channel).

This disadvantage can effectively be avoided by a nozzle having a recess as described above.

Figure 14:
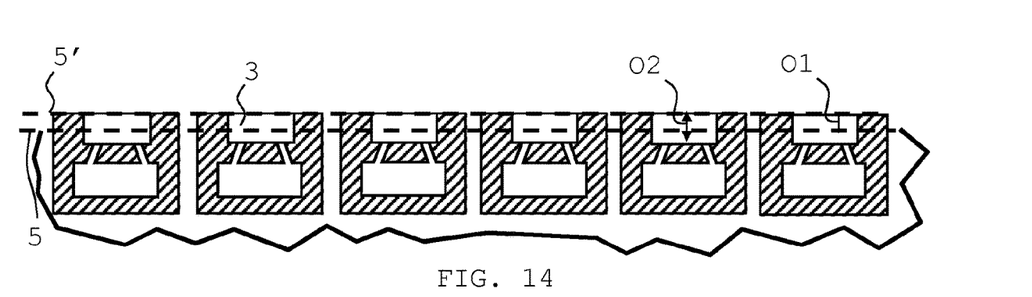
FIG. 14 shows a plurality of nozzle bodies according to the invention before being separated along an offset separation line.

As can be seen in FIG. 14, an offset between optimal separation line 5' and real separation line 5 does not affect the channel exit positions or channel lengths (reference numerals omitted), unless the offset O1 is larger than the length of the recess 3 (offset O2).

Figure 15:
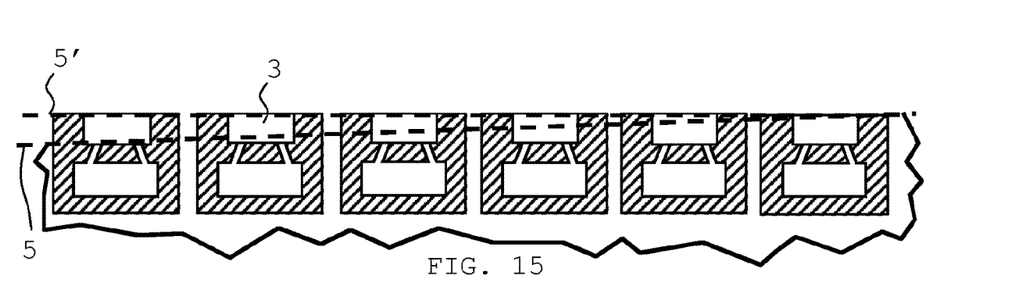
FIG. 15 shows a plurality of nozzle bodies according to the invention before being separated along an angled separation line.

Also, as can be seen in FIG. 15, an angular deviation of separation line 5 does not affect the positions or lengths of the channels exits, as long as the separation line 5 crosses the recess 3 of each nozzle body.

The following is a list of numbered items comprised by the present invention:
1. Nozzle for an inhalation device for nebulizing a liquid into a respirable aerosol, with a nozzle body (1) which has a front end (1B) and which comprises at least two ejection channels (2, 2'), each channel (2, 2') having an channel exit (2A, 2A'), wherein the ejection channels two channels (2, 2'), and which has a front end (4B) that is, in a view perpendicular to a longitudinal axis (X) of the nozzle body (1), congruent with the front end (1B) of the nozzle body (1), and wherein said recess (3) has a first depth (D') which is larger than the depth (D) of said at least two channels (2, 2').
2. Nozzle according to item 1, wherein at least two recesses (3) are provided, and wherein in each of the two recesses only one channel exit (2A, 2A') is located.
3. Nozzle according to item 1 or 2, wherein the nozzle body (1) is a monolithic structure.
4. Nozzle according to any of the preceding items, wherein the recess (3) further has a portion (3') which extends into the lid (4).
5. Nozzle according to any of the preceding items, wherein said recess (3) has, seen along longitudinal axis (X), an increasing depth (D') and/or width (W'), such that a sloping cross section is provided, being widest at the front end (1B, 4B).
6. Nozzle according to any of the preceding items, comprising a plurality of nozzle bodies (1).
7. Nozzle according to item 6, wherein each nozzle body (1) has its own recess (3).
8. Nozzle according to item 6, wherein multiple nozzle bodies (1) share a common recess (3).
9. Nozzle according to any of the preceding items, wherein a side opposite to the flat side (1A) of one nozzle body (1) serves as lid (4) for an adjoining nozzle body (1).
10. Nozzle according to any one of items 4 to 9, wherein the lid (4) provides the upper portion (3') of the recess (3), and wherein said portion (3') runs from one side of the lid (4) to the other side.
11. Nozzle according to item 10, wherein the recess portion (3') has the shape of a chamfer, with a channel-adjoining edge (6).
12. Method for the fabrication of a nozzle according to any of the preceding items, the method comprising the steps of
    a) providing a nozzle body (1) which has a front end (1B) and which comprises at least two ejection channels (2, 2'), each channel (2, 2') having an channel exit (2A, 2A'), wherein the ejection channels (2, 2') are arranged such as to eject liquid along respective ejection trajectories which intersect with one another at a collision point, wherein at least one recess (3) is provided at the front end (1B) in which at least two of the channel exits (2A, 2A') are positioned, wherein the nozzle body (1) has a flat side (1A), with the at least two liquid channels (2, 2') being entrenched with a defined depth (D) on said flat side (1A), comprising the following steps:
    providing a wafer substrate;
    fabricating on one side (1A) of said substrate at least two liquid channels (2, 2'), said channels (2, 2') having a defined depth (D);
    fabricating a recess (3) with a first depth (D') which is larger than the depth (D) of said at least two liquid channels (2, 2') in said one side (1A) of the body (1), said recess covering an end portion of the channels (2, 2');
    separating said body (1) from the substrate along a separation line (5) which crosses said recess (3);
    such that at least two channel exits (2B, 2B') in said recess (3) are obtained, wherein the distance between said channel exits (2A, 2A') remains unaffected by a possible angular or linear deviation of said separation line (5) from an optimal separation line (5'), and
    b) covering said nozzle body (1) with a lid (4).
13. Method according to item 12, wherein the lid (4) covers the at least two channels (2, 2'), and which has a front end (4B) that is, in a view perpendicular to a longitudinal axis (X) of the nozzle body (1), congruent with the front end (1B) of the nozzle body (1).
14. Method according to item 12 or 13, wherein a pattern representing a plurality of nozzle bodies (1) is batch fabricated in said wafer substrate, and wherein the separation line (5) crosses all recesses (3).
15. Method according to any one of items 12 to 14, wherein the nozzle is batch-fabricated from a wafer substrate.
16. Method according to any one of items 12 to 15, wherein the wafer substrate comprises or consists of a brittle material such as silicon, glass, or ceramics.
17. Method according to any one of items 12 to 15, wherein the wafer substrate comprises or consists of polyether ether ketone (PEEK).
18. Nozzle according to any one of items 1 to 11, wherein the nozzle is batch-fabricated from a wafer substrate.
19. Nozzle according to any one of items 1 to 11 or 18, wherein the wafer substrate comprises or consists of a brittle material such as silicon, glass, or ceramics.
20. Nozzle according to any one of items 1 to 11 or 18 to 19, wherein the wafer substrate comprises or consists of polyether ether ketone (PEEK).
21. Nozzle according to any of items 1 to 11 or 18 to 20, obtained or obtainable by a process according to any one of claims 12 to 17.
22. Use of a nozzle according to any of items 1 to 11 or 18 to 21 in an inhalation device for nebulizing a liquid into a respirable aerosol.
23. Inhalation device for nebulizing a liquid into a respirable aerosol, comprising a nozzle according to any of items 1 to 11 or 18 to 21.

LIST OF REFERENCES 1 nozzle body
1A flat side
1B front end
1C front end comprising region
2, 2' ejection channel, liquid channel, channel
2A, 2A' channel exit
2B, 2B' front end channel exit
3 recess
3' upper portion of recess
4 lid
4B front end
5 separation line
5' optimal separation line
6 edge
D depth
D' depth
W' width
A, A' jet axis
X longitudinal axis
Y, Y' lateral distance
O1, O2 offset
α angle
P plane

What is claimed is:

1. Method for the fabrication of a nozzle for an inhalation device for nebulizing a liquid into a respirable aerosol, the method comprising the steps of:
   a) providing a nozzle body which has a front end and which comprises at least two ejection channels, each channel having a channel exit, wherein the at least two ejection channels are arranged such as to eject the liquid along respective ejection trajectories which intersect with one another at a collision point, wherein at least one recess is provided at the front end in which at least two of the channel exits are positioned, wherein the nozzle body has a flat side, with the at least two ejection channels being entrenched with a defined depth on said flat side, comprising the following steps:
   providing a wafer substrate;
   fabricating, on one side of said substrate, the at least two ejection channels, said at least two ejection channels having the defined depth;
   fabricating the at least one recess with a first depth which is larger than the depth of said at least two ejection channels in said flat side of the body, said at least one recess covering a front end portion of the at least two ejection channels;
   separating said nozzle body from the substrate along a separation line which crosses said at least one recess;
   such that at least two channel exits in said at least one recess are obtained, wherein the distance between said channel exits remains unaffected by a possible angular or linear deviation of said separation line from an optimal separation line, and
   b) covering said nozzle body with a lid.

2. Method according to claim 1, wherein the lid covers the at least two ejection channels, and which has the front end that is, in a view perpendicular to a longitudinal axis of the nozzle body, congruent with the front end of the nozzle body.

3. Method according to claim 1, wherein the nozzle body comprises a plurality of nozzle bodies, and wherein a pattern representing the plurality of nozzle bodies is batch fabricated in said wafer substrate, and wherein the separation line crosses all recesses of the plurality of nozzle bodies.

4. Method according to claim 3, wherein a side opposite to the flat side of one nozzle body of the plurality of nozzle bodies serves as a lid for an adjoining nozzle body.

5. Method according to claim 3, wherein each nozzle body has its own at least one recess.

6. Method according to claim 3, wherein multiple nozzle bodies share a common recess of the at least one recess.

7. Method according to claim 1, wherein the nozzle is batch-fabricated from the wafer substrate.

8. Method according to claim 7, wherein the wafer substrate comprises or consists of a brittle material.

9. Method according to claim 8, wherein the brittle material is silicon, glass, or ceramics.

10. Method according to claim 1, wherein the wafer substrate comprises or consists of polyether ether ketone (PEEK).

11. The nozzle fabricated by the method according to claim 1.

12. Method according to claim 1, wherein at least two recesses are provided, and wherein, in each of the two recesses, only one of the channel exits is located.

13. Method according to claim 1, wherein the nozzle body is a monolithic structure.

14. Method according to claim 1, wherein the at least one recess further has a portion which extends into the lid.

15. Method according to claim 1, wherein the at least one recess has, seen along a longitudinal axis, an increasing depth and/or width, such that a sloping cross section is provided, being widest at the front end.

16. Method according to claim 1, wherein the lid provides an upper portion of the at least one recess, and wherein the upper portion runs from one side of the lid to the other side.

17. Method according to claim 16, wherein the upper portion has the shape of a chamfer, with a channel-adjoining edge.

* * * * *